US010278855B2

United States Patent
Salido, III

(10) Patent No.: US 10,278,855 B2
(45) Date of Patent: May 7, 2019

(54) FINGER SPLINT FOR TREATING BOUTONNIERE DEFORMITY

(71) Applicant: Albert Rojo Salido, III, Lower Lake, CA (US)

(72) Inventor: Albert Rojo Salido, III, Lower Lake, CA (US)

(\*) Notice: Subject to any disclaimer, the term of this patent is extended or adjusted under 35 U.S.C. 154(b) by 285 days.

(21) Appl. No.: 15/462,267

(22) Filed: Mar. 17, 2017

(65) Prior Publication Data

US 2017/0281386 A1  Oct. 5, 2017

Related U.S. Application Data

(60) Provisional application No. 62/315,355, filed on Mar. 30, 2016.

(51) Int. Cl.
*A61F 5/01* (2006.01)
*A61F 5/10* (2006.01)
*A61F 5/058* (2006.01)

(52) U.S. Cl.
CPC .......... *A61F 5/013* (2013.01); *A61F 5/05875* (2013.01); *A61F 5/10* (2013.01); *A61F 2005/0172* (2013.01)

(58) Field of Classification Search
CPC ...... A61F 5/013; A61F 5/012; A61F 5/05875; A61F 5/10
See application file for complete search history.

(56) References Cited

U.S. PATENT DOCUMENTS

| | | | | |
|---|---|---|---|---|
| 2,357,323 | A * | 9/1944 | Goldberg | A61F 5/05866 602/21 |
| 3,794,019 | A * | 2/1974 | Ritland | A61F 5/10 602/22 |
| 5,328,448 | A * | 7/1994 | Gray, Sr. | A61F 5/013 482/44 |
| 5,376,091 | A * | 12/1994 | Hotchkiss | A61B 17/62 602/22 |
| 5,848,983 | A * | 12/1998 | Basaj | A61F 5/05866 602/22 |
| 8,012,108 | B2 * | 9/2011 | Bonutti | A61F 5/0102 601/33 |
| 8,038,637 | B2 * | 10/2011 | Bonutti | A61F 5/013 602/20 |
| 9,849,001 | B2 * | 12/2017 | Thompson, Jr. | A61F 2/586 |

\* cited by examiner

*Primary Examiner* — Kristen Matter

(57) ABSTRACT

A Finger Splint for treating boutonniere deformities is provided. The Finger Splint has a dual axis support mechanism that allows full flexure and extension of the finger while pressure is applied to correct the deformity.

1 Claim, 5 Drawing Sheets

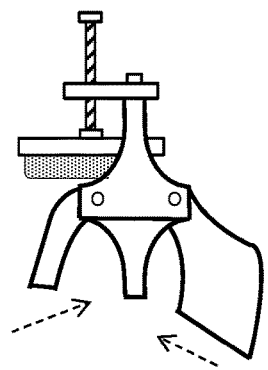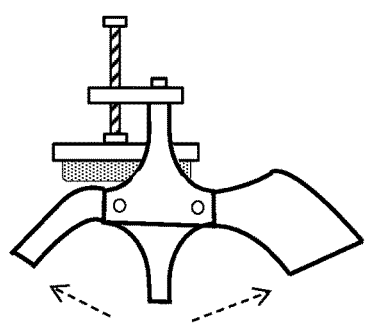
Fig. 2a  Fig. 2b
Fig. 2

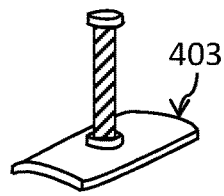
Fig. 4a
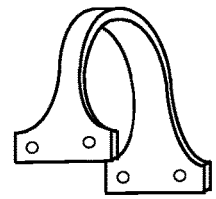
Fig. 4b
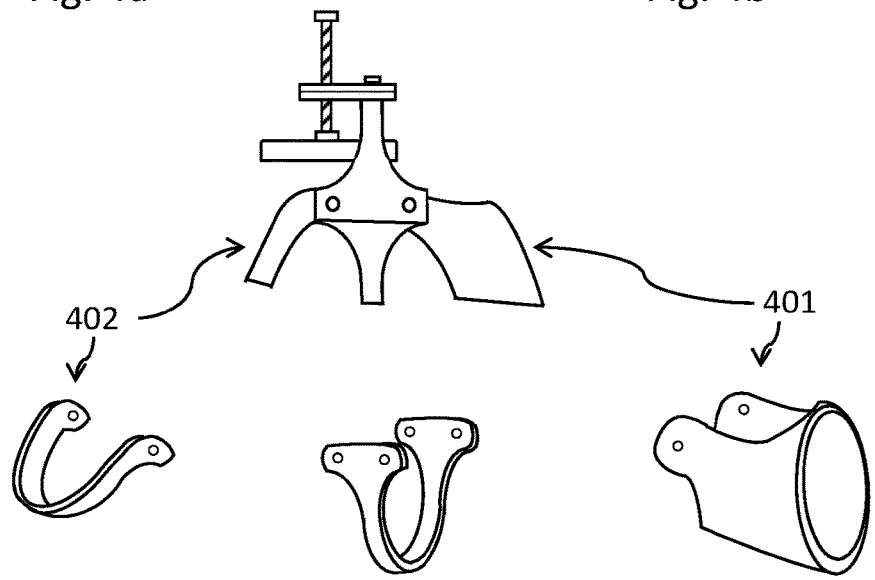
Fig. 4c  Fig. 4d  Fig. 4e
Fig. 4

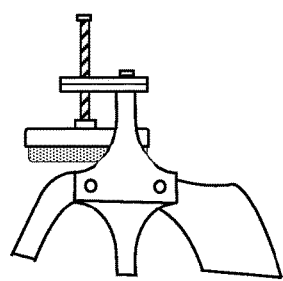
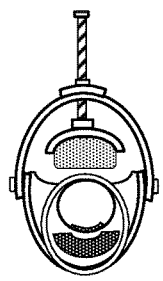
Fig. 5a  Fig. 5b
Fig. 5

FINGER SPLINT FOR TREATING BOUTONNIERE DEFORMITY

CROSS-REFERENCES TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND OF THE INVENTION

1. Field of the Invention

The present invention relates generally to orthopedic splints, and more particularly to finger splints for treating boutonniere deformities.

2. Description of the Related Art

A boutonniere deformity is a condition of the finger where the joint nearest the knuckle (the PIP joint) is bent toward the palm while the farthest joint (the DIP joint) is bent back away. This is called PIP flexion with DIP hyperextension. It can be caused by injury or conditions such as rheumatoid arthritis or Ehlers Danlos Syndrome. Such injuries and conditions are a common occurrence and are most often treated with splints that immobilize the finger. However, rendering a finger completely immobile during the course of healing is not always desirable. In particular, with a boutonniere deformity caused by injury, lack of movement of the joint can produce undesirable tendon contraction and inhibit rehabilitation. Although some splints that allow movement of the joint exist, the motion allowable is restricted to bending about a single axis, which prevents the finger from fully flexing. In addition, the splints that allow motion do not include any corrective means for the condition. It is an object of the present invention to provide a finger splint which allows full motion of the joint while also providing an adjustable external force to the deformed area. By applying external force to correct the condition while allowing flexure of the finger, rehabilitation of the condition can be greatly accelerated.

BRIEF SUMMARY OF THE INVENTION

The present invention is a finger splint comprised of a dual axis flexible finger support with an attached deformity correction device. The dual axis flexible finger support includes a proximal phalanx support and a distal phalanx support that are each rotatably connected to a frame. The deformity correction device is adjustably attached to the top of the frame and has a loosely attached pressure device for applying uniform force to the top of the finger. To use the device, the patient simply inserts the injured finger into the splint and then adjusts the pressure device until it is applying a comfortable pressure to the deformed joint. The patient can extend and contract the finger, rotating both the PIP and DIP joints. This extension and contraction while pressure is applied to the joint allows exercise of the tendons while correcting the condition.

BRIEF DESCRIPTION OF THE SEVERAL VIEWS OF THE DRAWINGS

A more complete understanding of the present invention may be derived by referring to the detailed description and claims when considered in connection with the figures, wherein like reference numbers refer to similar items throughout the figures, and:

FIG. 2 provides two side views of the Finger Splint showing it fully contracted (FIG. 2a) and fully expanded (FIG. 2b);

FIG. 4 provides perspective views of the various components of the device without padding components, specifically, FIG. 4a shows a perspective view of the finger plate, FIG. 4b shows a perspective view of the upper frame, FIG. 4c shows a perspective view of the proximal phalanx support, FIG. 4d shows a perspective view of the lower support, and FIG. 4e shows a perspective view of the distal phalanx support; and FIG. 5a provides a side view of the finger splint with the padding components and FIG. 5b provides a front view of the finger splint with the padding components.

DETAILED DESCRIPTION OF THE INVENTION

In the following detailed description of the invention, reference is made to the accompanying drawings which form a part of the disclosure and which show by way of illustration, and not of limitation, specific embodiments by which the invention may be practiced. The drawings, the foregoing discussion, and the following description are exemplary and explanatory only, and are not intended to limit the scope of the invention or its application in any manner.

The Finger Splint 101 is comprised of a Dual Axis Flexible Finger Support 102 with an attached Deformity Correction Device 103. The Dual Axis Flexible Finger Support 102 includes a Distal Phalanx Support 401 and a Proximal Phalanx Support 402 that are each rotatably connected to a Frame Assembly 301. The Frame Assembly 301 is shown separately in FIGS. 3c and 3d. The Phalanx Supports (401 and 402) are attached to the Frame Assembly 301 such that they can rotate independently about two different axes, allowing full contraction and extension of both the PIP and DIP finger joints, as shown in FIG. 2. The Frame Assembly 301 consists of a Lower Support 302, an Upper Frame 303, and a Bracket 304. Each component is preferably made of steel, but may also be made from suitably strong plastic. In an alternate embodiment, the Lower Support 302, Upper Frame 303 and Bracket 304 could be made from one or two pieces. In a preferred embodiment, the Lower Support 302 has an attached Lower Support Pad 305 that is made of foam, rubber, or other suitable material to provide a comfortable surface to support the patient's finger.

Figure 1:
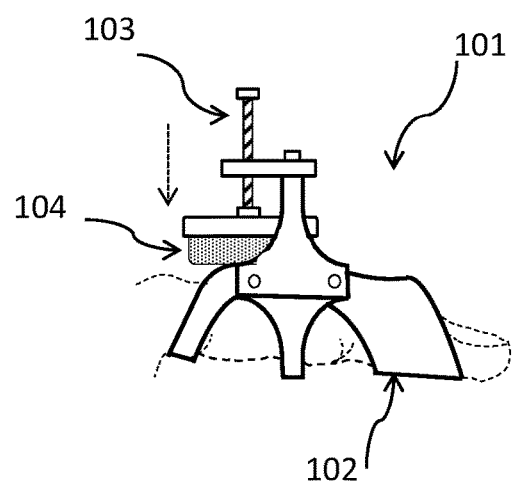
FIG. 1 is a side view of the Finger Splint shown with a finger inserted.
Figure 3:
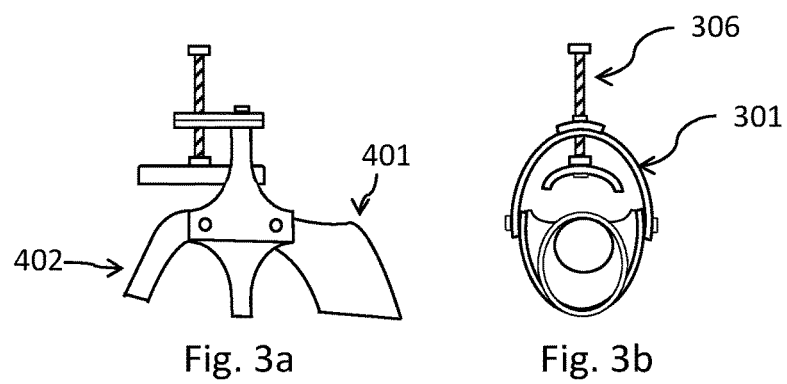
FIG. 3 provides a side view (FIG. 3a) and a front view (FIG. 3b) without the padding components, a front view with the padding components (FIG. 3e), and a side view (FIG. 3c) and a front view (FIG. 3d) of only the Frame Assembly with a padding component.
Figure 3:
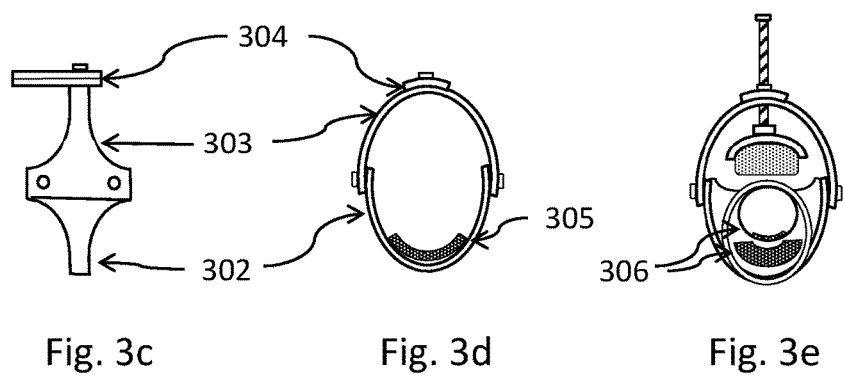

The Distal Phalanx Support 401 and Proximal Phalanx Support 402 are of suitable inner diameters to accommodate the distal phalanx and proximal phalanx, respectively, of the injured finger. They both preferably have Comfort Pads 306 made from foam, rubber, or other suitable cushioning material as shown in FIG. 3e.

The Deformity Correction Device 103 is adjustably attached to the Bracket 304 at the top of the Frame Assembly 301. In a preferred embodiment, the Deformity Correction Device 103 has a Threaded Part 306 that is screwed into a threaded hole in the Bracket 304 and a loosely attached Finger Plate 403 with a Finger Pad 104 made of foam, rubber or other suitable cushioning material attached to the bottom. The Finger Plate 403 is loosely attached to the Threaded Part 306 so that when the Threaded Part 306 is rotated, the Finger Plate 403 does not rotate relative to the patient's finger. In addition, in a preferred embodiment, the Finger Plate 403 has a small amount of axial play so that when it is pushed against the finger it angles to match the surface of the finger for the patient's comfort.

To use the device, the patient simply inserts the injured finger into the Finger Splint 101 and then adjusts the Deformity Correction Device 103 until it is applying a comfortable pressure to the injured joint. The patient can extend and contract the finger, rotating both the PIP and DIP joints. This extension and contraction while pressure is applied allows exercise of the tendons while correcting the condition.

Many modifications and variations of this invention may be made without departing from its spirit and scope, as will be appreciated by those skilled in the art. The embodiment as described herein was chosen and described in order to best explain the principles of the invention and its practiced applications.

What is claimed is:

1. A finger splint configured to mount to a finger to correct a boutonniere deformity, the splint comprising:
    a frame comprising a top side, a proximal phalanx support, a distal phalanx support, a deformity correction device, and a member configured to fit around the finger at an intermediate phalanx of the finger;
    wherein a top side of the member is configured to extend vertically above the finger;
    wherein the proximal phalanx support is connected to the frame so as to be rotatable in a bending direction of the finger and comprises a ring element configured to fit around the finger at a proximal phalanx of the finger;
    wherein the distal phalanx support is connected to the frame so as to be rotatable in a bending direction of the finger and comprises a ring element configured to fit around the finger at a distal phalanx of the finger; and
    wherein the deformity correction device comprises a finger plate and a connecting part, the connecting part being adjustably attached to the top side of the frame such that the finger plate can be moved vertically to engage the finger for applying an external force to correct the deformity while allowing flexure of the finger.

* * * * *